US00PP25468P2

(12) United States Plant Patent
Beck

(10) Patent No.: US PP25,468 P2
(45) Date of Patent: Apr. 28, 2015

(54) ***BETULA* TREE NAMED 'JEFPARK'**

(50) Latin Name: *Betula platyphylla*
Varietal Denomination: Jefpark

(71) Applicant: Dwayne Beck, Red Deer, CA (US)

(72) Inventor: Dwayne Beck, Red Deer, CA (US)

(73) Assignee: Jeffries Nurseries Ltd., Portage La Prairie (CA)

( * ) Notice: Subject to any disclaimer, the term of this patent is extended or adjusted under 35 U.S.C. 154(b) by 124 days.

(21) Appl. No.: 13/815,087

(22) Filed: Jan. 30, 2013

(51) Int. Cl.
*A01H 5/00* (2006.01)

(52) U.S. Cl.
USPC ..... Plt./216

(58) Field of Classification Search
CPC ..... A01H 5/00
USPC ..... Plt./216
See application file for complete search history.

(56) References Cited

PUBLICATIONS

PLUTO UPOVPROM Plant Variety Database Citation for 'Jefpark' as per CA PBR 11-7318; Jun. 30, 2011.*

* cited by examiner

*Primary Examiner* — Kent L Bell
(74) *Attorney, Agent, or Firm* — Penny J. Aguirre

(57) ABSTRACT

A new cultivar of *Betula* tree, 'Jefpark', that is characterized by its narrowly columnar and ellipsoidal plant habit and its compact plant habit, and its dense branching with lateral branch angles of less than 45° to vertical.

2 Drawing Sheets

Genus/species: *Betula platyphylla.*
Varietal denomination: 'Jefpark'.

BACKGROUND OF THE INVENTION

The present invention relates to a new and distinct cultivar of *Betula platyphylla* and will be referred to hereafter by its cultivar name, 'Jefpark'. 'Jefpark' represents a new cultivar of Asian white-birch, a deciduous tree grown for landscape use.

The Inventor discovered the new cultivar in summer of 2006 as a naturally occurring branch mutation of *Betula platyphylla* 'Fargo' (U.S. Plant Pat. No. 10,963) that was growing in a field row at a nursery in Red Deer, Alberta, Canada.

Asexual propagation of the new cultivar was first accomplished by in vitro propagation under the direction of the Inventor in Elnora, Alberta, Canada in summer of 2006. Asexual propagation by in vitro propagation has determined that the characteristics of the new cultivar are stable and are reproduced true to type in successive generations.

SUMMARY OF THE INVENTION

The following traits have been repeatedly observed and represent the characteristics of the new *Betula*. These attributes in combination distinguish 'Jefpark' as unique and distinct cultivar of *Betula.*

1. 'Jefpark' exhibits a narrowly columnar and ellipsoidal plant habit.
2. 'Jefpark' exhibits dense branching with lateral branch angles of less than 45° to vertical.

'Fargo', the parent plant of 'Jefpark', differs from 'Jefpark' in having a conical plant habit and in having wider branch angles. 'Jefpark' can also be compared to the cultivar 'VerDale' (U.S. Plant Pat. No. 15,944) and 'Whitespire' (not patented). 'Verdale' differs from 'Jefpark' in being taller and wider (more pyramidal in habit) and in having golden fall color. 'Whitespire' differs from 'Jefpark' in having a pyramidal plant habit with wider lateral branch angles.

BRIEF DESCRIPTION OF THE DRAWING

The accompanying photographs were taken of three year-old plants of 'Jefpark' as grown outdoors in a Portage la Prairie, Manitoba, Canada, The photograph in FIG. 1 was taken of 5 year-old field grown plants of 'Jefpark' and provides a view of the plant habit of 'Jefpark'.

The photograph in FIG. 2 was taken of 4 year-old plants as grown in 39-liter containers and provides a comparison between 'Jefpark' (row on left) and 'Fargo' (two rows on right).

Figure 1:
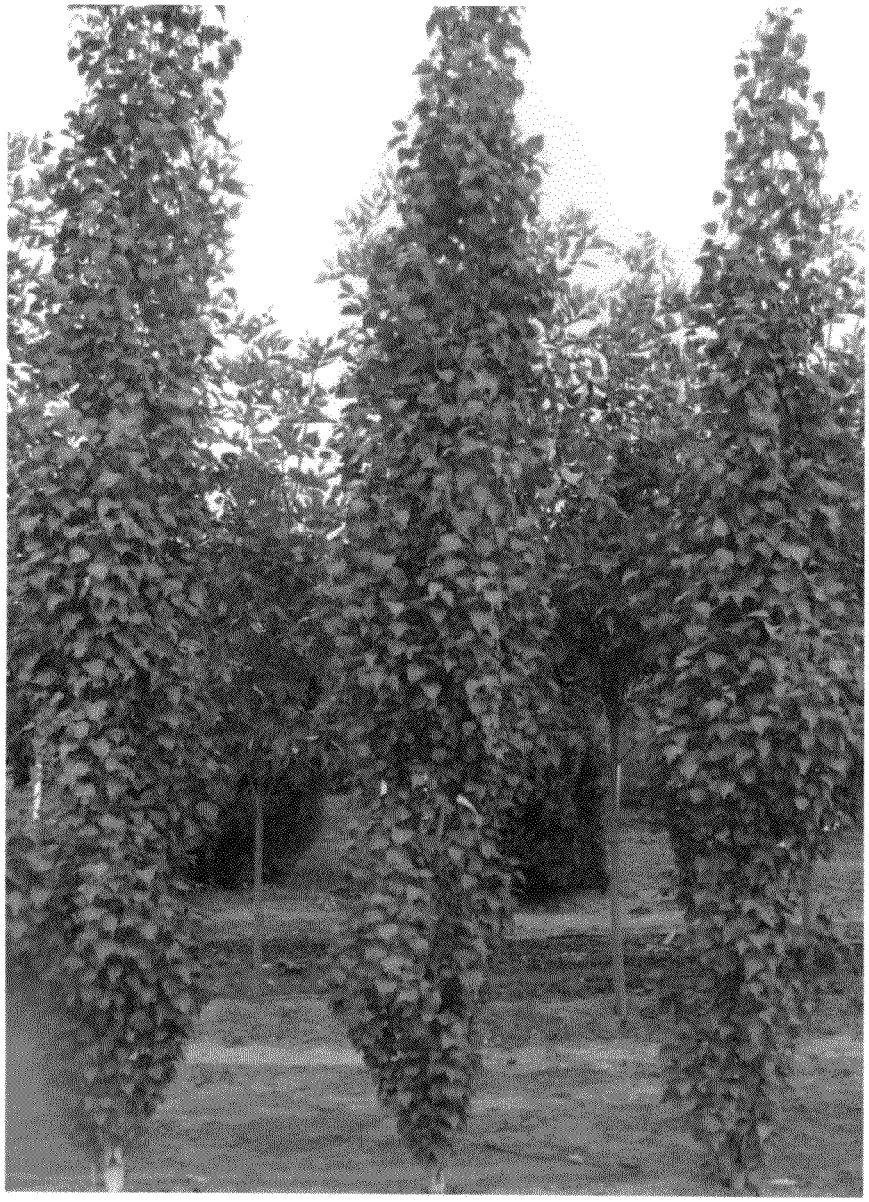
Figure 2:
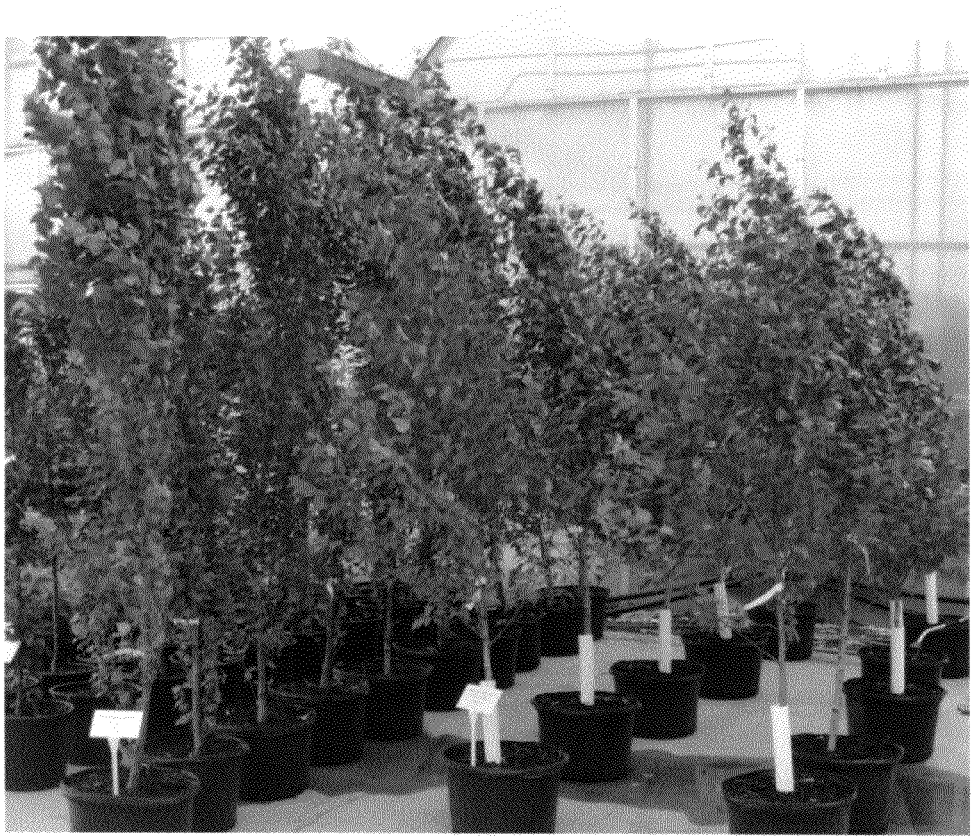

The colors in the photographs are as close as possible with the digital photography and printing techniques utilized and the color codes in the detailed botanical description accurately describe the colors of the new *Betula.*

BOTANICAL DESCRIPTION OF THE PLANT

The following is a detailed description of four year-old plants of the new cultivar as grown outdoors in 10-gallon containers in Portage la Prairie, Manitoba, Canada. Phenotypic differences may be observed with variations in environmental, climatic, and cultural conditions. The color determination is in accordance with The 2007 R.H.S. Colour Chart of The Royal Horticultural Society, London, England, except where general color terms of ordinary dictionary significance are used.

General description:

*Plant habit.*—Deciduous tree.

*Plant habit.*—Narrowly columnar and ellipsoidal.

*Height and spread.*—An average of 3.6 m in height and 40 cm in spread (4 year-old plant), mature trees reach about 9 m in height and 1.5 m in spread.

*Hardiness.*—At least in U.S.D.A. Zones 2 to 4.

*Diseases.*—No particular susceptibility or resistance has been observed.

*Growth rate.*—Moderate.

Branch description:

*Trunk size.*—Average of 3.2 cm in diameter measured 120 cm from soil line.

*Stem color.*—New growth (shoots) 145A with very small lenticels 166A in color, old growth twigs 166A with lenticels 156D, bark 197B to 197C suffused with N199C.

*Stem shape.*—Round.

*Stem size.*—Main stems; average of 6 cm in diameter and 65 cm in length (including peduncle), lateral branches; average of 1.5 mm in diameter and 25 cm in length, tertiary branches; an average of 15 cm in length and 3 mm in diameter.

*Stem surface.*—New growth; glabrous, glaucous, and lenticillate, old growth twigs; glabrous, shiny, glaucescent, lenticillate, mature bark; dull and exfoliating.

*Branching.*—Densely branched; an average of 7 lateral branches with an average of 4 tertiary branches per lateral branch, lateral branch angles are less than 45° from vertical.

*Buds.*—4 cm in length and 1 cm in width, 138B with 138D towards tip and 165A at apex in color, conical in shape with pointed apex, glabrous surface.

*Internode length.*—Main stems; 5 to 20 cm, lateral stems; an average of 3.5 cm.

Foliage description:

*Leaf shape.*—Deltoid.

*Leaf division.*—Simple.

*Leaf base.*—Obtuse.

*Leaf apex.*—Acuminate.

*Leaf venation.*—Pinnate, not conspicuous, color N144D on upper and lower leaf surface.

*Leaf margin.*—Biserrate.

*Leaf attachment.*—Petiolate.

*Leaf arrangement*—Alternate.

*Leaf surface.*—Glabrous on upper and lower surface.

*Leaf size.*—An average of 6 cm in length and 5.5 mm in width.

*Leaf internode length.*—An average of 3 cm.

*Leaf color.*—New growth upper and lower surface; 144A and suffused with 178A when emerging, mature foliage upper surface; N137B to N137C, mature foliage lower surface; 137B to 137C, new growth upper and lower surface; 144A, mature foliage upper surface; N137B to N137C, mature foliage lower surface; 137B to 137C, fall foliage upper and lower surface; 162A.

*Petioles.*—Average of 1.5 cm in length and 1 cm in width, round in shape, 145A in color, surface glabrous and glaucescent.

Flower description:

*Inflorescence.*—Monoecious, cylindrical male and female catkins, male catkins develop during the summer and fall, persistent through winter, opening in the spring, female catkins; spring in Manitoba, Canada.

*Catkins.*—Penduolous and cylindrical in shape, male; an average of 5 cm in length and 9 mm in diameter, scales; winged, an average 6 mm in length and 5.5 mm in width, apex; cuspidate, base; gladiate, 144B in color transitioning to 145D at the base, an average of 400 flowers per catkin, stamens not observed female; an average of 1.9 cm in length and 7 mm in diameter, scales; winged, an average of 3.5 mm in length and 4.5 mm in width, apex; cuspidate, base; truncate, 144A in color, and average of 200 flowers per catkin, pistils not observed.

*Flower type.*—Imperfect.

*Flower fragrance.*—None.

*Flower lastingness.*—Female catkins mature into fall, male catkins present fall through spring.

*Flower buds.*—Ovate in shape, an average of 1.5 mm in width and 3 mm in height, 143A in color.

*Peduncles.*—An average of 1.5 cm in length and 1 mm in diameter, 144A lightly suffused with 174A in color, glabrous surface.

*Pedicels.*—Sessile.

*Perianth.*—Not present.

*Fruit and seed.*—Winged nutlet; an average of 4.5 mm in width and 3 mm in height; 165B in color, wings translucent.

It is claimed:

1. A new and distinct cultivar of *Betula* tree named 'Jefpark' substantially as herein illustrated and described.

* * * * *